United States Patent [19]

Easton et al.

[11]  4,344,967
[45]  Aug. 17, 1982

[54] FILM FORMING COMPOSITION AND USES THEREOF

[75] Inventors: Ian A. Easton, Glasgow, Scotland; James M. Glen; Ann G. Kieran, both of Bathurst, Australia

[73] Assignee: Devro, Inc., Somerville, N.J.

[21] Appl. No.: 174,313

[22] Filed: Aug. 1, 1980

[30] Foreign Application Priority Data

Aug. 7, 1979 [GB] United Kingdom ................. 7927460

[51] Int. Cl.$^3$ ............................................. A61K 47/00
[52] U.S. Cl. .................................................... 424/359
[58] Field of Search ................. 106/136; 424/360, 177

[56] References Cited

U.S. PATENT DOCUMENTS

| | | | |
|---|---|---|---|
| 1,809,082 | 5/1927 | Urkov et al. | 424/360 |
| 2,128,296 | 8/1938 | Goodwin et al. | 106/136 |
| 2,143,868 | 1/1939 | Dexheimer | 106/136 |
| 2,354,319 | 1/1942 | Inman | 424/360 |
| 3,042,524 | 7/1962 | Albus et al. | 106/136 |
| 4,199,564 | 4/1980 | Silver et al. | 424/360 |

Primary Examiner—Delbert R. Phillips

[57] ABSTRACT

A film-forming composition comprises a stable aqueous solution of a protein hydrolysate, e.g. a partially hydrolysed collagen protein, preferably having a molecular weight of from 3,000 to 45,000, glycerol and optionally a water-miscible solvent. The composition may be used to form a protective barrier on skin, e.g. one or more teats of a cow.

5 Claims, No Drawings

FILM FORMING COMPOSITION AND USES THEREOF

This invention relates to a film-forming composition, and to uses thereof in treating human or animal skin, particularly in a method of forming a protective barrier film around one or more teats of a cow.

Lactating cows are susceptible to two forms of teat infection, namely mastitis and teat hacks, both of which can lead to damaged teats, milk loss and in severe cases the loss of the cow. Immediately after a cow has been milked the teat duct is open and remains open for about an hour. It is during this time that infection can enter the teat and lead to high cell counts in the milk. The hacking problem occurs during the summer months and is caused by the teat skin drying out. Milking machine cups cause cracks in the skin and during the summer flies attack the open sores and strip relatively large areas of skin which then become infected.

Teat dips based on cellulose derivatives and bactericidal creams have not proved effective as they do not remain long enough on the teat and do not prevent fluid loss from the sore.

U.S. Pat. No. 3,548,056 discloses lotion and detergent compositions characterized by mild effect upon skin and to a process of prophylactically protecting skin from detergent irritation. The compositions comprise an inert solvent and incorporated therein a water-soluble surface active agent and a water-soluble, partially degraded protein having a gel strength of about zero Bloom grams. Water-immiscible materials may be present, and when they are employed, the compositions are particularly useful as skin lotions.

U.S. Pat. No. 3,767,784 discloses a method for treating diseased or injured abraded, lacerated or ulcerated body tissue, which comprises applying thereto to thereby provide a temporary nucleus to facilitate growth of replacement tissues for healing purposes, a soft and flexible gelled soluble dressing, filling or cementing composition consisting essentially of an effective local therapeutic amount of a carbohydrate such as a saccharide and an effective tissue repair promoting local amount of a proteinaceous gel-forming material such as gelatin.

U.S. Pat. No. 4,094,973 discloses a therapeutic agent comprising a non-antigenic protein hydrolysate having polypeptides and amino acids derived from immature animal protein such as chicken feet by mild acid hydrolysis. This is spray dried or otherwise dewatered or concentrated to a dry powder or dried gel. In use, the powder is topically applied to a moist open wound, or is reconstituted with water and injected, with a syringe, into the area to be treated.

The present invention provides a film-forming composition comprising a stable aqueous solution of a protein hydrolysate and glycerol, and, optionally, a water-miscible solvent, e.g. ethanol.

The application of a coating of a film-forming composition in accordance with the present invention to skin, e.g. one or more teats provides, after drying, a protective barrier film which seals the skin, e.g. teat(s), from the ambient atmosphere.

Preferably said protein hydrolysate is a partially hydrolysed collagen protein. Preferably the molecular weight is from 3,000 to 45,000. In this molecular weight range the collagen hydrolysate is film-forming but non-gelling.

The collagen hydrolysate used in preparing the film-forming composition preferably has a pH of from 4.5 to 5.0, and further preferably has a solids concentration of from 30 to 60% by weight, most preferably 55% by weight. The final film-forming composition preferably comprises 25 to 75%, more preferably 25 to 40%, by weight hydrolysate solids, most preferably 32% by weight.

Preferably the glycerol content of the film-forming composition is from 1 to 10% by weight, most preferably 2% by weight.

When ethanol is used in the film-forming composition of the present invention, 5 to 54% by weight, most preferably 40% by weight, of industrial methylated spirit (95%) may be employed.

The present invention further provides a method of treating human or animal skin, e.g. forming a protective barrier film around one or more teats of a cow, comprising applying a coating of a film-forming composition in accordance with the present invention to said skin, e.g. teat(s), and effecting drying of said coating.

The protective barrier film temporarily seals the teat duct or open sore, reducing fluid loss therefrom, while forming a physical barrier to micro-organisms and insect attack. The film is continuous and flexible, remains on the teat between milking intervals, and yet is easily washed off with warm water immediately prior to milking. The composition from which the film is formed is relatively quick drying to seal the teat duct or sore in a few minutes.

The film-forming composition of the present invention can be used to treat skin lesions, e.g. open sores, in other animal species and humans. As the film is preferably derived from an animal source, i.e. collagen, it contains polypeptide "building blocks" which should take part in the natural healing process without rejection problems. A sore covered with a protein derivative will allow the natural phagocytic wound cleaning process to take place at the skin surface.

The present invention even further provides a teat-shaped protective barrier film comprising a protein hydrolysate, preferably collagen hydrolysate, and glycerol (glycerin).

Film-forming compositions in accordance with the present invention may include further ingredients such as anti-microbial agents, e.g. bactericidal agents. A dye, e.g. Crystal Violet, may be added to the protein hydrolysate to allow optical identification of the area treated.

A preferred embodiment of a film-forming composition in accordance with the present invention and its use in forming a protective barrier film around a cow's teats will now be described by way of example.

EXAMPLE

A collagen hydrolysate is prepared from comminuted limed bovine hide at 15% solids and is broken down initially to gelatin by cooking at 15 p.s.i. and 120° C. for three hours. The gelatin solution is cooled at 65° C. and adjusted in pH to 7.5 to 8 with dilute sulphuric acid. Trypsin enzyme at 0.4% based on the collagen solids is added at 65° C. Enzyme digestion at 65° C. is continued for two hours, and then the enzyme activity is destroyed by a second thermal treatment at 15 p.s.i. and 120° C. for 45 minutes. The pH of the resulting solution is adjusted with dilute sulphuric acid to 4.5 to 4.8 and the solution allowed to stand for several hours. Most of the fat and elastin separates out as a result of the pH adjustment, leaving a cloudy amber liquid of about 15% solids. The liquid is filtered through a series of fine filters until a clear solution is obtained. The solution is then evaporated under vacuum to 55% solids. Any remaining calcium emanating from the limed hide precipitates and is removed. The hydrolysate produced having a molecular weight in the range 3000 to 45,000 is to be distinguished from gelatin which has a considerably higher molecular weight.

The pH of the initial gelatin solution can also be adjusted to 7.5 to 8.0 with hydrochloric acid and the final pH of the solution reduced to pH 4.5 to 5.0 with hydrochloric acid. When hydrochloric acid is used there is no precipitate of the calcium salt to be filtered from the concentrated hydrolysate.

The hydrolysate solution is then mixed with industrial methylated spirits (95%) and glycerol to give a final composition of hydrolysate solids 32%, industrial methylated spirits 40%, glycerol 2%, and water 26% in the form of a stable aqueous solution. A small addition of dye such as Crystal Violet may be made to give an identifying colour to show the teats which have been treated. This solution has a viscosity which makes it easy to apply to the teats, but does not readily run off. The application of a coating of the solution to the teats can be by dipping or spraying. Spraying tends to be less efficient than dipping which is rapid and covers the teat efficiently. After coating the teats, they are allowed to dry, or if desired, forced drying is employed. The composition dried to a film in about ten minutes.

The hydrolysate solution per se forms a hard brittle film when dry (it does not form a gel) and is slow drying. Glycerol operates as a softening agent or plasticiser to make the film soft and flexible, and will help to keep the teat skin soft. To assist the drying rate of the film, various water-miscible solvents may be used, but the best solvent found in terms of solution stability and drying characteristics is industrial methylated spirits (95%)

We believe that the film-forming composition of the present invention finds possible use in providing a protective barrier film on animal or human skin, whether or not afflicted with skin lesions such as sores or wounds, and accordingly from this aspect of the present invention a method of forming a protective barrier film on human or animal skin comprises applying a coating of a film-forming composition in accordance with the present invention, and effecting drying of said coating.

Although, as indicated above, the dip method is more convenient for application of a film-forming composition of the present invention to cows' teats, the film-forming composition may be used in a sprayable form as, for example, in an aerosol or other pressure spray gun.

The molecular weight of the protein hydrolysate referred to above was determined by SEPHADEX Gel Column Chromatography.

We claim:

1. A non-gelling, film-forming composition comprising a stable aqueous solution containing 25% to 40% by weight of partially hydrolysed collagen protein solids having a molecular weight of from 3,000 to 45,000 and from 1% to 10% by weight glycerol.

2. A composition of claim 1 further comprising a water-miscible solvent.

3. A composition according to claim 2 wherein the solvent is ethanol.

4. A method of treating human or animal skin comprising applying a coating of a non-gelling, film-forming composition comprising a stable aqueous solution containing 25% to 40% by weight of partially hydrolysed collagen protein solids having a molecular weight of from 3,000 to 45,000 and from 1% to 10% by weight glycerol to said skin, and effecting drying of said coating to form a film.

5. A method of forming a protective barrier film around one or more teats of a cow comprising applying a coating of a non-gelling, film-forming composition comprising a stable aqueous solution containing 25% to 40% by weight of partially hydrolysed collagen protein solids having a molecular weight of from 3,000 to 45,000 and from 1% to 10% by weight glycerol to said teat(s) and effecting drying of said coating to form said protective barrier film.

* * * * *